US008983108B2

(12) United States Patent
Ho

(10) Patent No.: US 8,983,108 B2
(45) Date of Patent: Mar. 17, 2015

(54) EAR HEADPHONE

(71) Applicant: Dexin Corporation, New Taipei (TW)

(72) Inventor: Shin-Chuan Ho, New Taipei (TW)

(73) Assignee: Dexin Corporation, New Taipei (TW)

( * ) Notice: Subject to any disclaimer, the term of this patent is extended or adjusted under 35 U.S.C. 154(b) by 0 days.

(21) Appl. No.: 13/944,952

(22) Filed: Jul. 18, 2013

(65) Prior Publication Data

US 2015/0023541 A1 Jan. 22, 2015

(51) Int. Cl.
*H04R 25/00* (2006.01)
*H04R 1/10* (2006.01)
*A61B 7/02* (2006.01)

(52) U.S. Cl.
CPC .................................... *H04R 1/1058* (2013.01)
USPC ............................ 381/380; 381/328; 181/135

(58) Field of Classification Search
CPC ...... H04R 1/10; H04R 1/1008; H04R 1/1016; H04R 1/105; H04R 1/1075
USPC ......... 381/182, 370–376, 380, 309, 328, 329; 181/129, 130, 135
See application file for complete search history.

(56) References Cited

U.S. PATENT DOCUMENTS 4,712,245 A * 12/1987 Lyregaard ..................... 381/324
6,585,075 B1 * 7/2003 Gauthier ........................ 181/135
8,050,437 B2 * 11/2011 Feeley et al. .................. 381/322
2010/0166245 A1 * 7/2010 Takigawa et al. ............. 381/380

* cited by examiner

*Primary Examiner* — Amal Zenati
*Assistant Examiner* — Sunita Joshi
(74) *Attorney, Agent, or Firm* — Li & Cai Intellectual Property (USA) Office

(57) ABSTRACT

The in ear headphone includes a main body, an ear pad and a speaker. The main body includes a first wall and a second wall. The first wall defines a chamber, and the first and second walls collectively define a gap. One end of the gap and one end of the chamber are both directed toward an ear canal. The other end of the gap is directed toward surrounding air. The ear pad corresponds to one end of the gap and the chamber. The ear pad conformingly contacts the ear canal. The speaker is disposed in the chamber.

10 Claims, 10 Drawing Sheets

EAR HEADPHONE

BACKGROUND OF THE INVENTION

1. Field of the Invention

The instant disclosure relates to an in ear headphone; in particular, to an in ear headphone communicable to the ambient sound by a channel.

2. Description of Related Art

In ear headphones allow audio components to be inserted to the ear canal. However, the in ear headphone provides audio insulation once a user puts on the earphone and the ambient sound is blocked. If a user uses the earphone when walking, the traditional in ear headphone isolates the listener from external sound, for example, horn, and it may lead to traffic accident.

To address the above issues, the inventor strives via associated experience and research to present the instant disclosure, which can effectively improve upon the limitation described above.

BRIEF SUMMARY OF THE INVENTION

The instant disclosure provides an in ear headphone communicable to the ambient sound.

According to one exemplary embodiment of the instant disclosure, the in ear headphone includes a main body, an ear pad and a speaker. The main body includes a first wall and a second wall. The first wall defines a chamber, and the first and second walls collectively define a gap. One end of the gap and one end of the chamber are both directed toward an ear canal. The other end of the gap is directed toward ambient air. The ear pad corresponds to one end of the gap and the chamber. The ear pad conformingly contacts the ear canal. The speaker is disposed in the chamber.

The in ear headphone permits ambient sound even when wearing the earphone.

In order to further understand the instant disclosure, the following embodiments are provided along with illustrations to facilitate the appreciation of the instant disclosure; however, the appended drawings are merely provided for reference and illustration, without any intention to be used for limiting the scope of the instant disclosure.

DETAILED DESCRIPTION OF THE INVENTION

The aforementioned illustrations and following detailed descriptions are exemplary for the purpose of further explaining the scope of the instant disclosure. Other objectives and advantages related to the instant disclosure will be illustrated in the subsequent descriptions and appended drawings.

Figure 1:
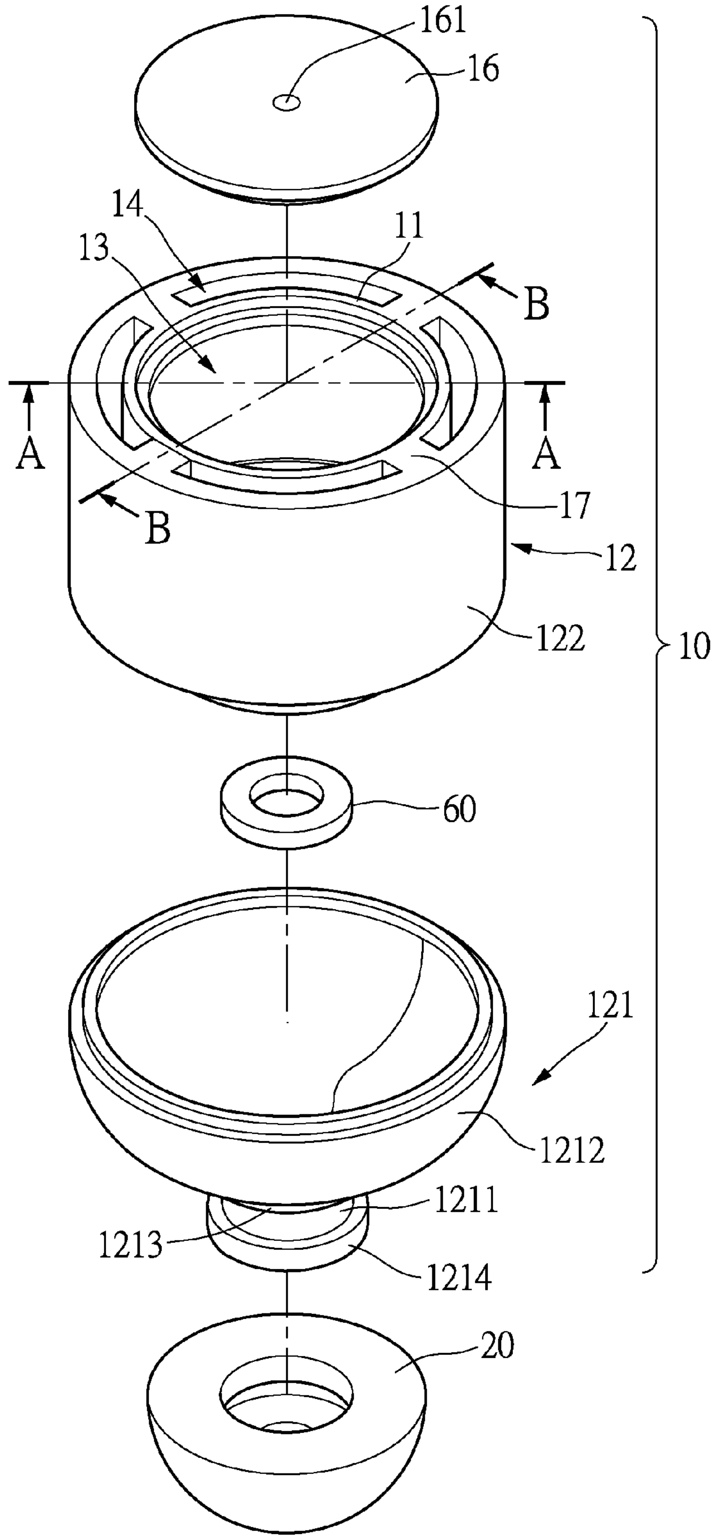
FIG. 1 is an exploded perspective view of an in ear headphone of the instant disclosure.

Please refer to FIG. 1 showing an exploded perspective view of an in ear headphone 1 of the instant disclosure. The in ear headphone 1 includes a main body 10, an ear pad 20 and a speaker 30 (referring to FIG. 4). The speaker 30 is disposed in the main body 10 (referring to FIG. 4). The ear pad 20 is formed with an opening 21 (referring to FIG. 2). The ear pad 20 encloses one end of the main body 10 through the opening 21. The ear pad 20 can be plugged into the user's ear canal (not shown) and the sound from the speaker 30 passes through the opening 21 to the user. The ear pad 20 is made of flexible and soft materials, for example, silicone gel or high density sponge. The material can be chosen according to cost, sound quality, comfort and the other associated factors. The contour of the ear pad 20 conformingly contacts the listener's ear canal. Because of the material of the ear pad 20, the ear pad 20 firmly and comfortably secures the earphone to the ear canal and cancels off ambient noise.

Figure 3:
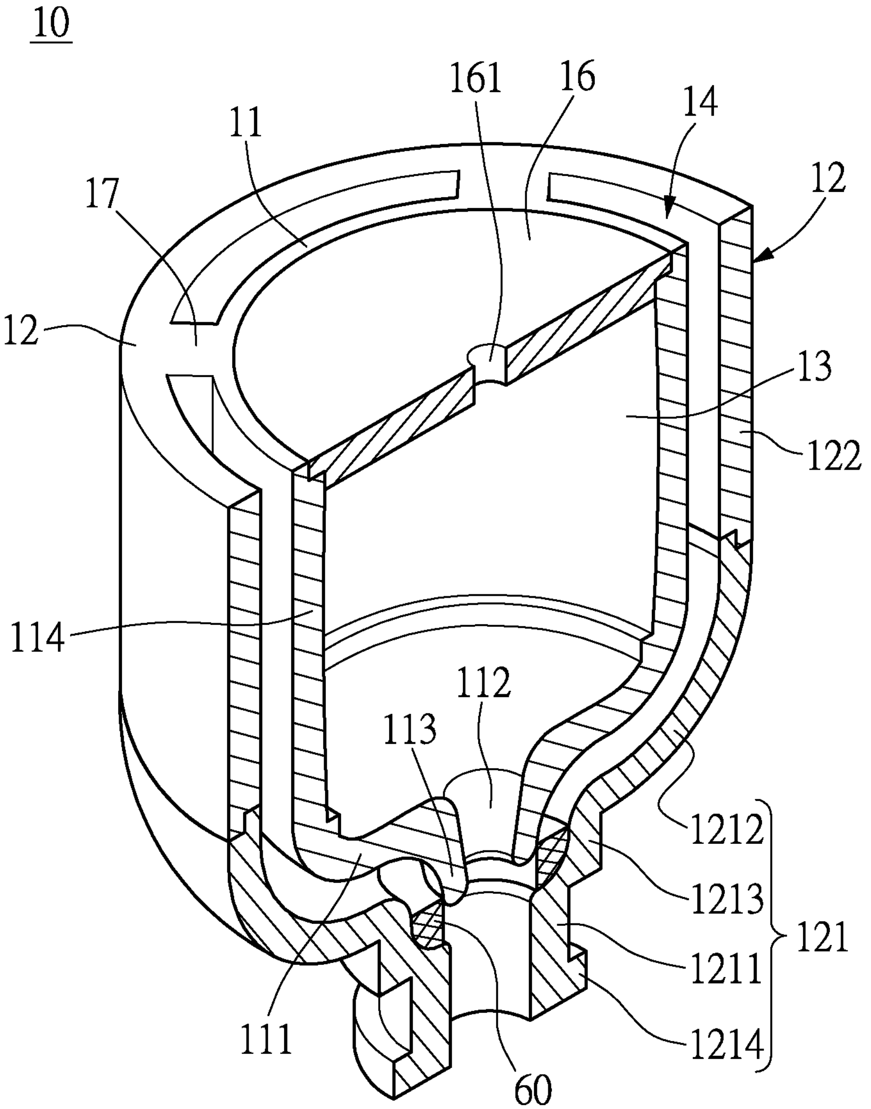
FIG. 3 is a perspective cross-sectional view along A-A of FIG. 1.
Figure 4:
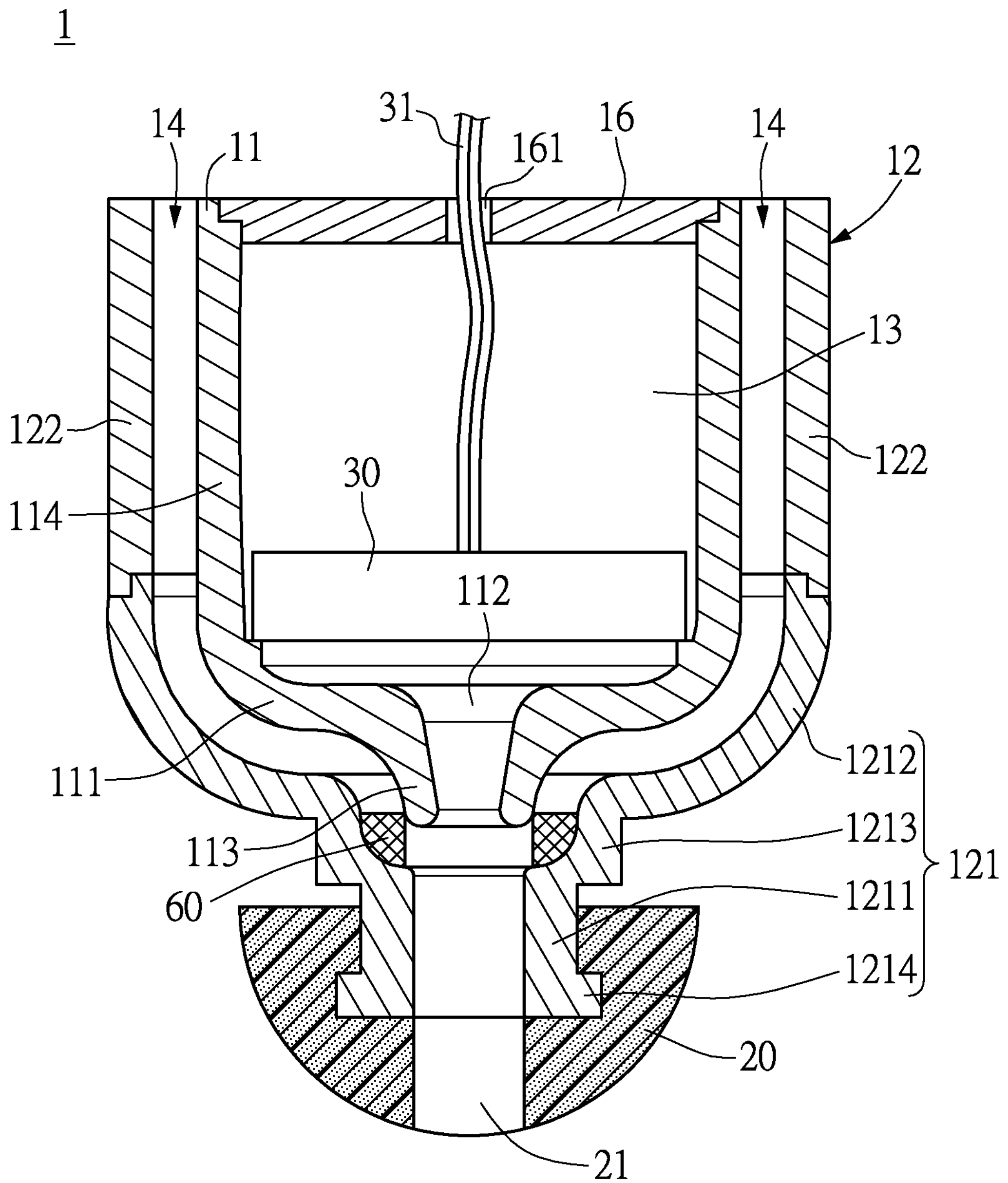
FIG. 4 is a schematic cross-sectional view along A-A of FIG. 1.
Figure 5:
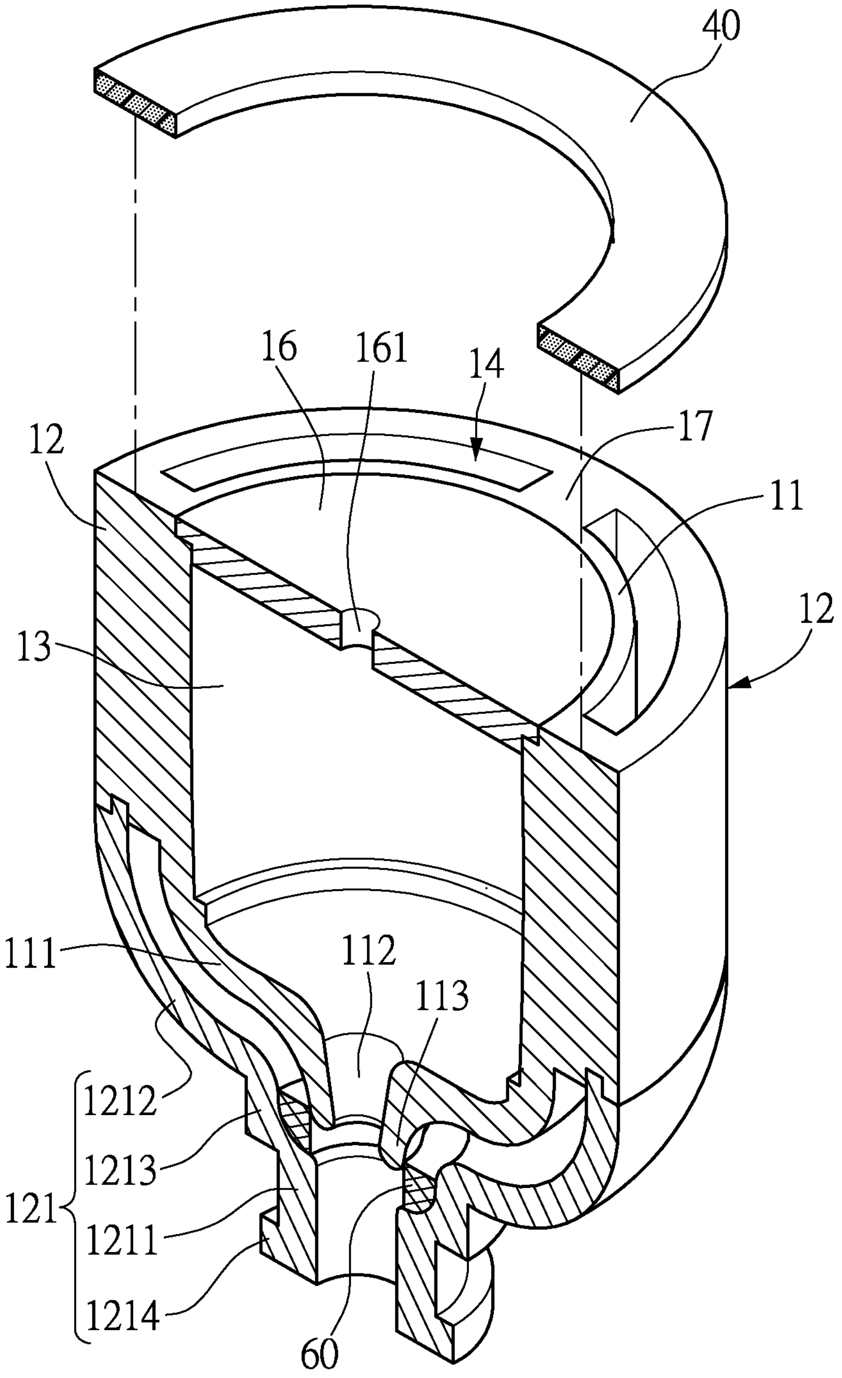
FIG. 5 is a perspective cross-sectional view along B-B of FIG. 1.
Figure 6:
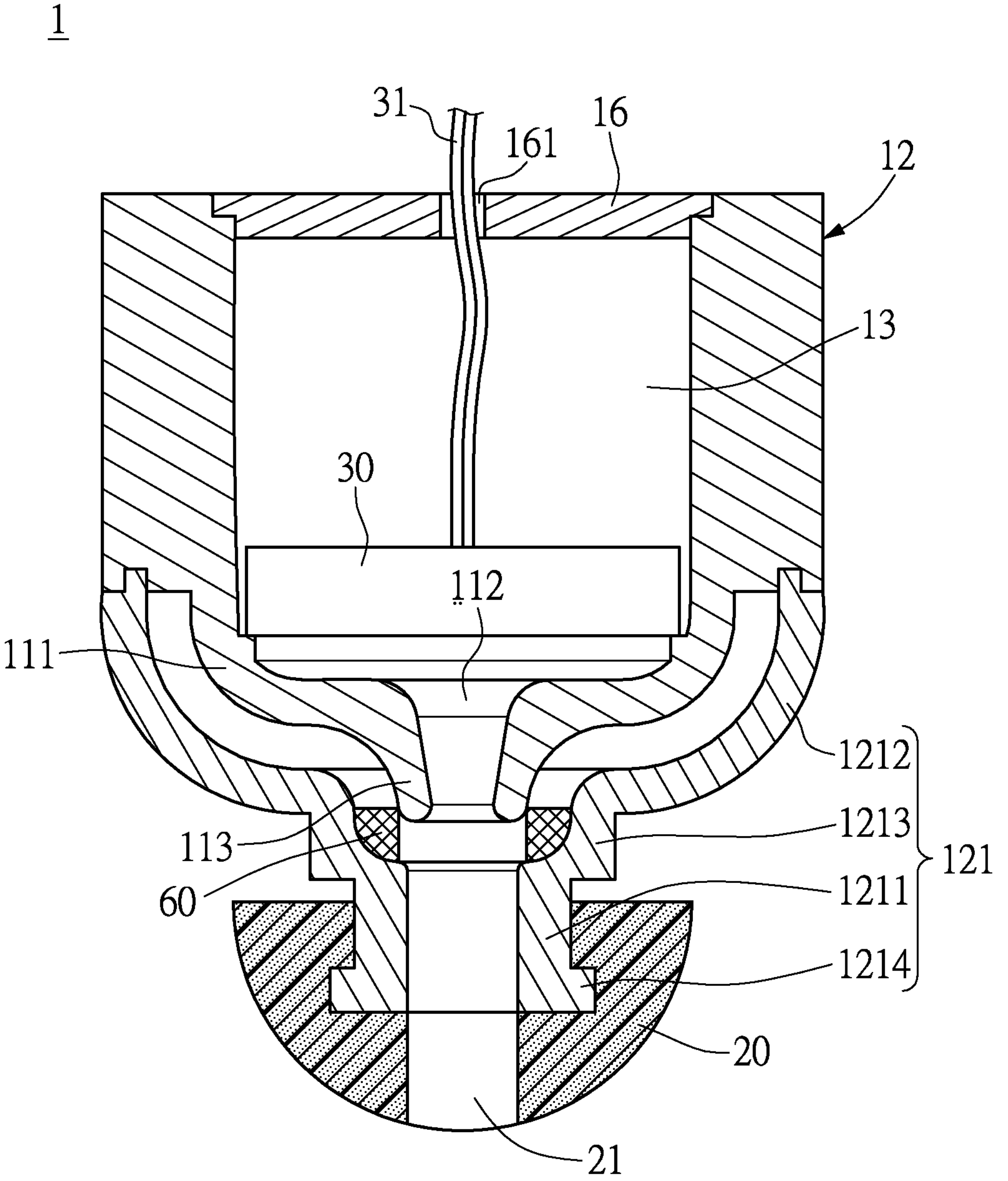
FIG. 6 is a schematic cross-sectional view along B-B of FIG. 1.
Figure 9:
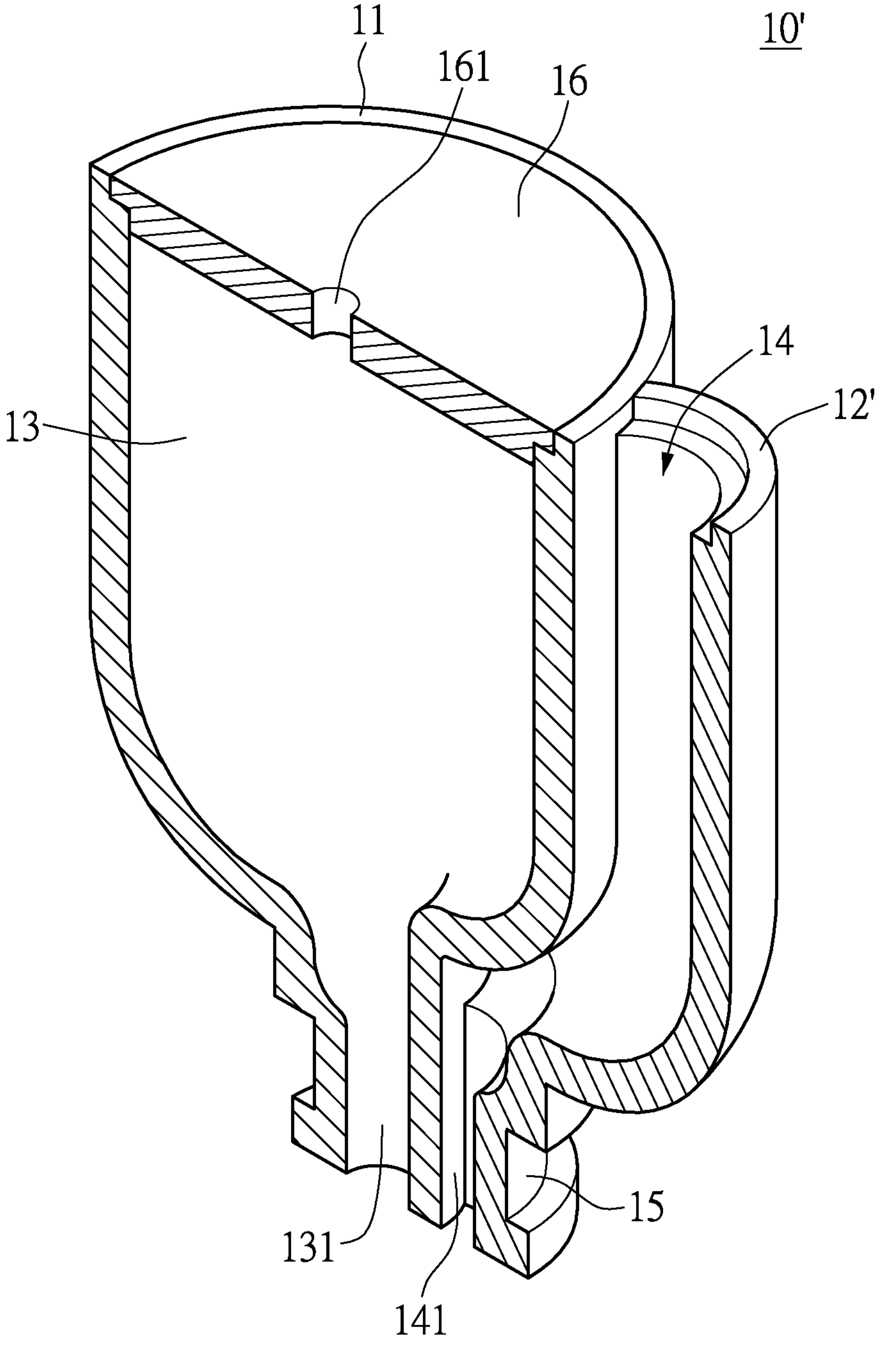
FIG. 9 is a perspective cross-sectional view along C-C of FIG. 8.
Figure 10:
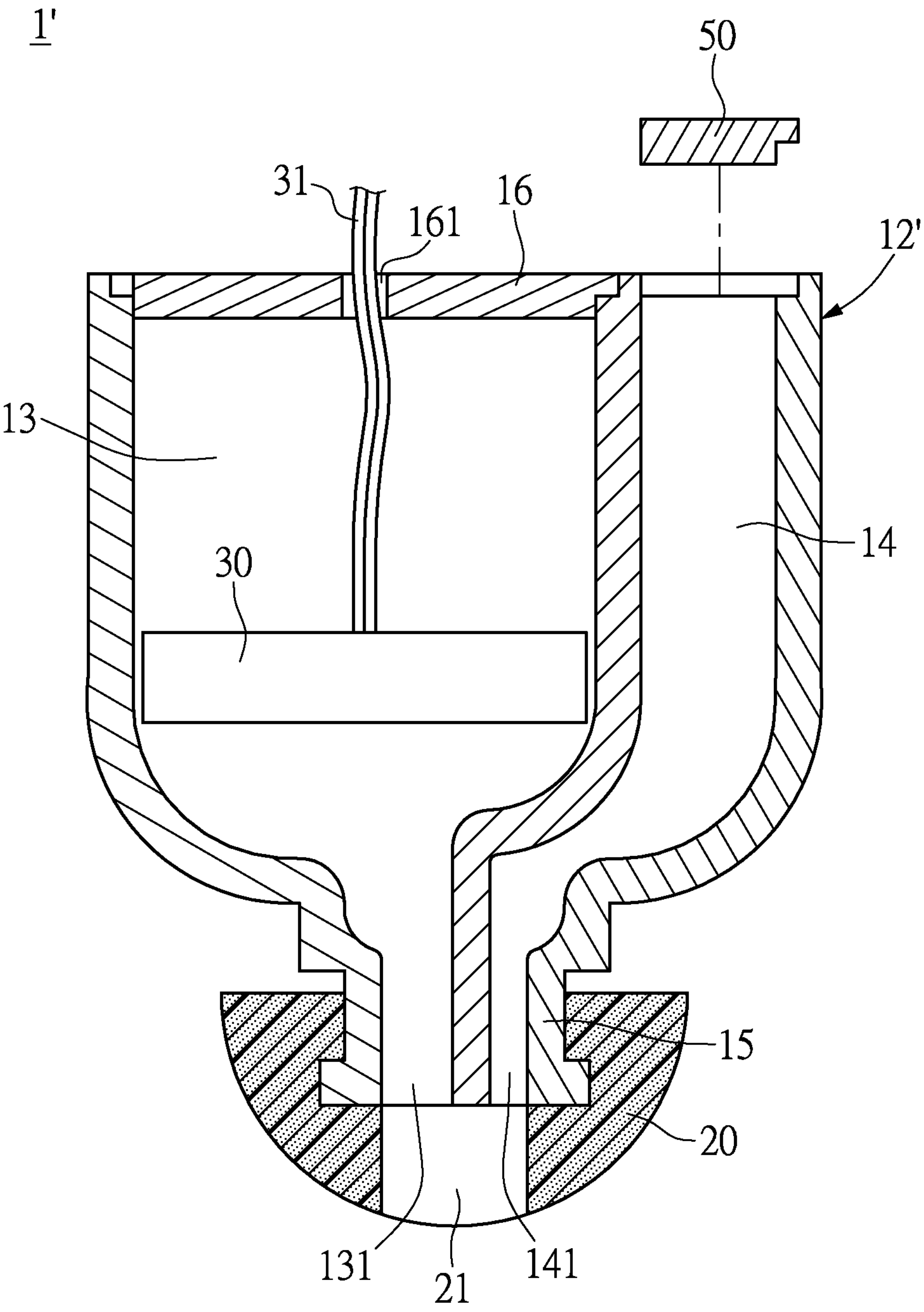
FIG. 10 is a schematic cross-sectional view along C-C of FIG. 8.

For clarity, the speaker 30 is shown in FIGS. 4, 6 and 10. The ear pad 20 is not shown in FIGS. 3, 5 and 9 but FIGS. 4, 6 and 10.

Figure 2:
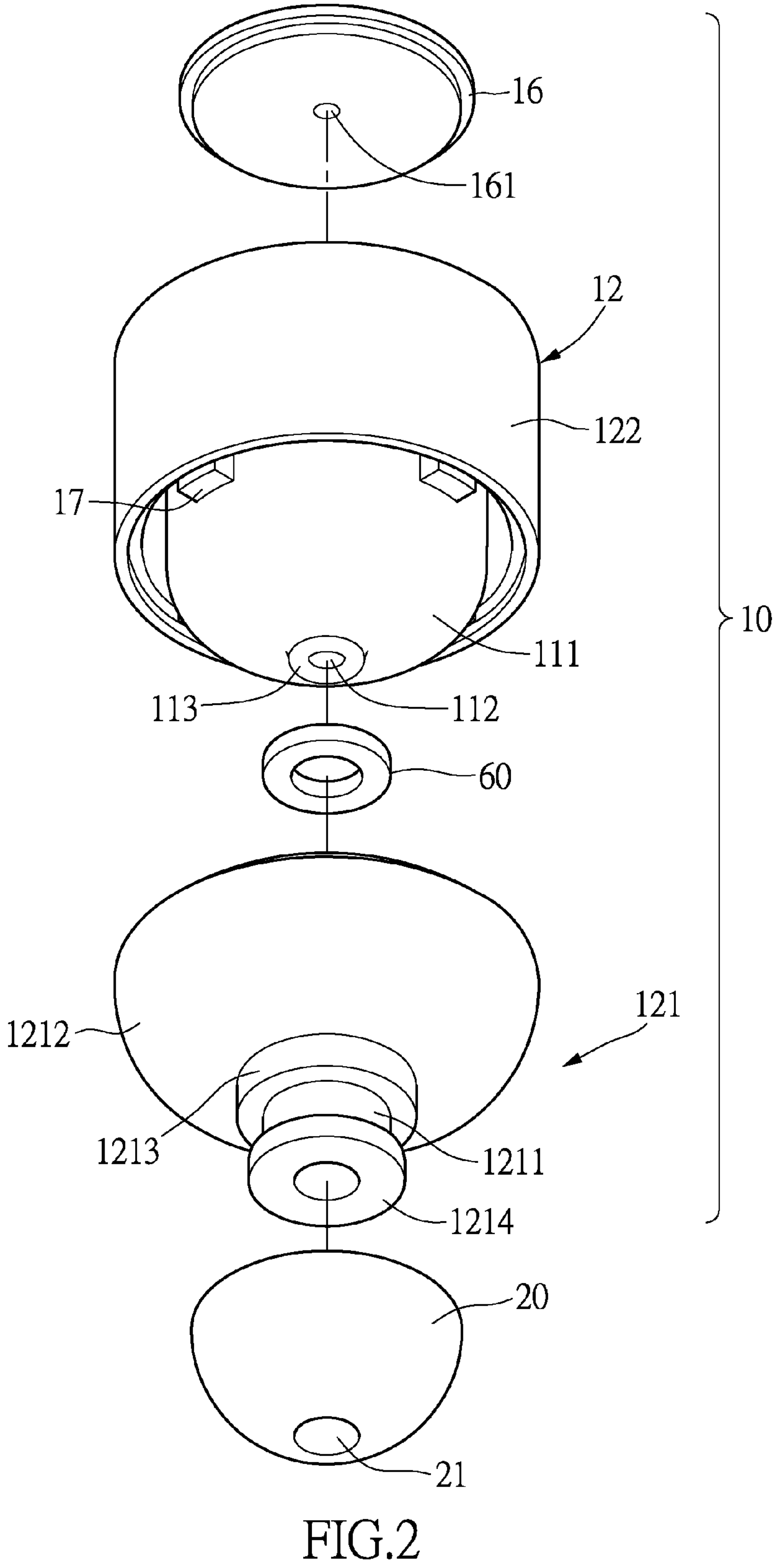
FIG. 2 is an exploded perspective view from another viewing point of the in ear headphone of the instant disclosure.

FIG. 2 shows an exploded perspective view from another viewing point of the in ear headphone of the instant disclosure. Referring to FIGS. 1 and 2, the main body 10 includes a first wall 11, a second wall 12, a lid 16 and a plurality of connection blocks 17. The connection blocks 17 connect the first and second walls 11, 12 and a gap 14 is formed therebetween. The first wall 11 defines a chamber 13. The gap 14 and the chamber 13 communicate sound toward the ear canal. One end of the gap 14 is communicable to external environment and therefore the ambient sound can be delivered therefrom. The lid 16 covers one end of the chamber 13 that is directed toward the ambient air.

In a first embodiment of the instant disclosure, the first and second walls 11, 12 are substantially concentric. The first wall 11 is spaced apart from the second wall 12 and the gap 14 is formed. The first wall 11 defines the chamber 13.

FIG. 3 is a perspective cross-sectional view along A-A of FIG. 1. FIG. 4 is a schematic cross-sectional view along A-A of FIG. 1. Referring to FIGS. 3 and 4, the first wall 11 is substantially tubular and the chamber 13 is defined by the tubular first wall 11. Each of the two ends of the first wall 11 is not sealed and as a result the chamber 13 opens at the two ends. However, the lid 16 seals one end of the first wall 11 that directs toward the ambient air. The first wall 11 is reduced toward the ear canal to form a curved portion 111. The curved portion 111 does not close the first wall 111 and therefore defines an outlet 112. An inner tube 113 is formed by the extension of the first wall 11 from the outlet 112 toward the ear canal. The inner diameter of the outlet 112 is smaller than that of the chamber 13 while the inner tube 113 is further reduced toward the ear canal to concentrate the sound wave.

Referring to FIGS. 3 and 4, the second wall 12 includes a adapter portion 121 and a tube portion 122. The adapter portion 121 is coupled to the end of the tube portion 122 that directs toward the ear canal. The adapter portion 121 resembles a funnel. The adapter portion 121 has a tapered portion 1212, a ring portion 1213 and a sound channel 1211.

The larger end of the tapered portion 1212 is coupled to the tube portion 122. The smaller end of the tapered portion 1212 extends toward the ear canal to form the ring portion 1213. The ring portion 1213 further extends toward the direction of ear channel to form the sound channel 1211. The ring portion 1213 has an inner diameter substantially similar to the smallest inner diameter of the tapered portion 1212 while the sound channel 1211 has an inner diameter smaller than the inner diameter of the ring portion 1213. In the instant embodiment, a step 1214 is formed proximate to the ear canal on the circumferential portion of the sound channel 1211. Additionally, the adapter portion 121 and the tube portion 122 are individually fabricated, allowing easier manufacturing and assembly.

The inner diameter of the tube portion 122 is larger than the outer diameter of the first wall 11. The inner diameter of the tapered portion 1212 of the adapter portion 121 is larger than the outer diameter of the curved portion 111. The inner diameter of the ring portion 1213 is larger than the outer diameter of the inner tube 113. Because of the diameter difference between the first wall 11 and the tube portion 122, the gap 14 is created therebetween. Similarly, the curved portion 111 is disposed in the tapered portion 1212 with a space formed therebetween. The inner tube 13 is disposed in the ring portion 1213 with a space formed therebetween. The space between the curved portion 111 and the tapered portion 1212 and the space between the inner tube 113 and the ring portion 1213 are communicable to the gap 14. The width of the gap 14 is smaller than the inner diameter of the chamber 13. However, the width of the gap 14 may vary according to the design of the earphone.

FIG. 5 is a perspective cross-sectional view along B-B of FIG. 1. FIG. 6 is a schematic cross-sectional view along B-B of FIG. 1. Referring to FIGS. 2, 5 and 6, the connection blocs 17 are evenly spaced and disposed between the first wall 11 and the tube portion 122 of the second wall 12. The first and second walls 11, 12 are then concentric while spaced apart. The lid 16 is formed with an aperture 161. The lid 16 covers the end of the chamber 13 that is directed toward the surrounding air. In other words, the lid 16 substantially seals one end of the chamber 13.

Figure 7:
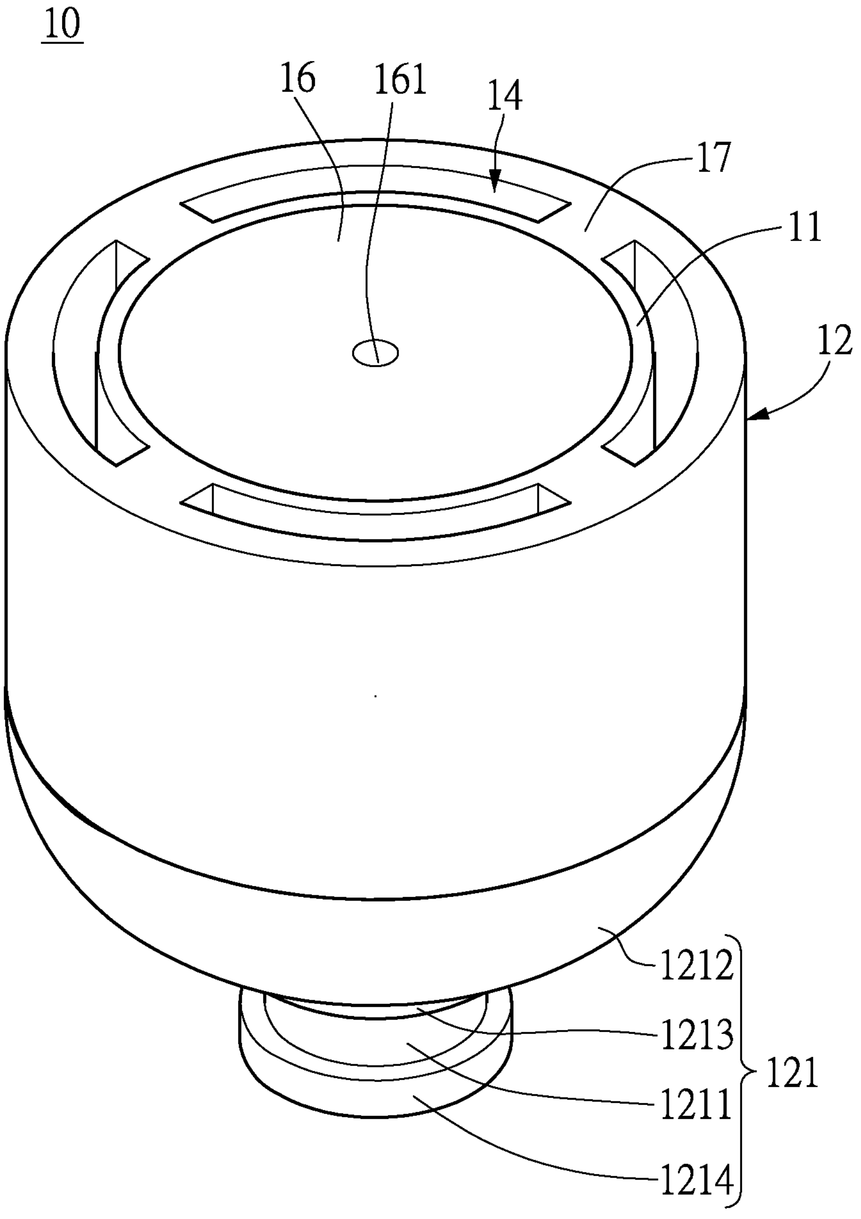
FIG. 7 is a schematic assembly diagram illustrating a main body of the in ear headphone of the instant disclosure.

FIG. 7 is a schematic assembly diagram illustrating the main body 10. Referring to FIGS. 3, 4 and 7, the speaker 30 is connected to a cord 31. The cord 31 connects to an electronic device and transmits signal to the speaker 30, causing a transducer (not shown) of the speaker 30 to vibrate. The speaker 30 is disposed in the chamber 13 proximate to the curved portion 111. The cord 31 goes through the aperture 161 of the lid 16. The ear pad 20 sleeves the sound channel 1211 through the opening 21. The step 1214 of the sound channel 1211 further stabilizes the engagement between the ear pad 20 and the sound channel 1211. The driving method of the speaker 30 may vary among coil, electrostatic, armature or the like according to cost, frequency, sound quality and life span.

The ear pad 20 is conformingly attached to and seals the ear canal such that the air pressure of the space created between the speaker 30 and the ear canal may vary. The transducer (not shown) of the speaker 30 vibrates because of the signal received by the speaker 30. The chamber 13 and the space between the speaker 30 and the ear canal have different air pressure to create sounds and return the transducer.

The sound created by the speaker 30 enters the inner tube 113 through the outlet 112 and then to the sound channel 1211. The ambient sound enters from one end of the gap 14 to the inner 113 and then the sound channel 1211. The sound propagates to the ear canal through the opening 21 of the ear pad. Because the inner diameter of the inner tube 113 reduces gradually, the sound from the speaker 30 is more concentrated and the ambient sound from the gap 14 does not interfere therewith. Furthermore, the first wall 11 segregates the chamber 13 and the gap 14 so that the chamber 13 is substantially closed to prevent audio leakage. The width of the gap 14 is relatively short, and in addition to allowing the ambient sound, the aforementioned air pressure may be adjusted as well. The width of the gap 14 may vary according to the dimension of the speaker 30.

Figure 8:
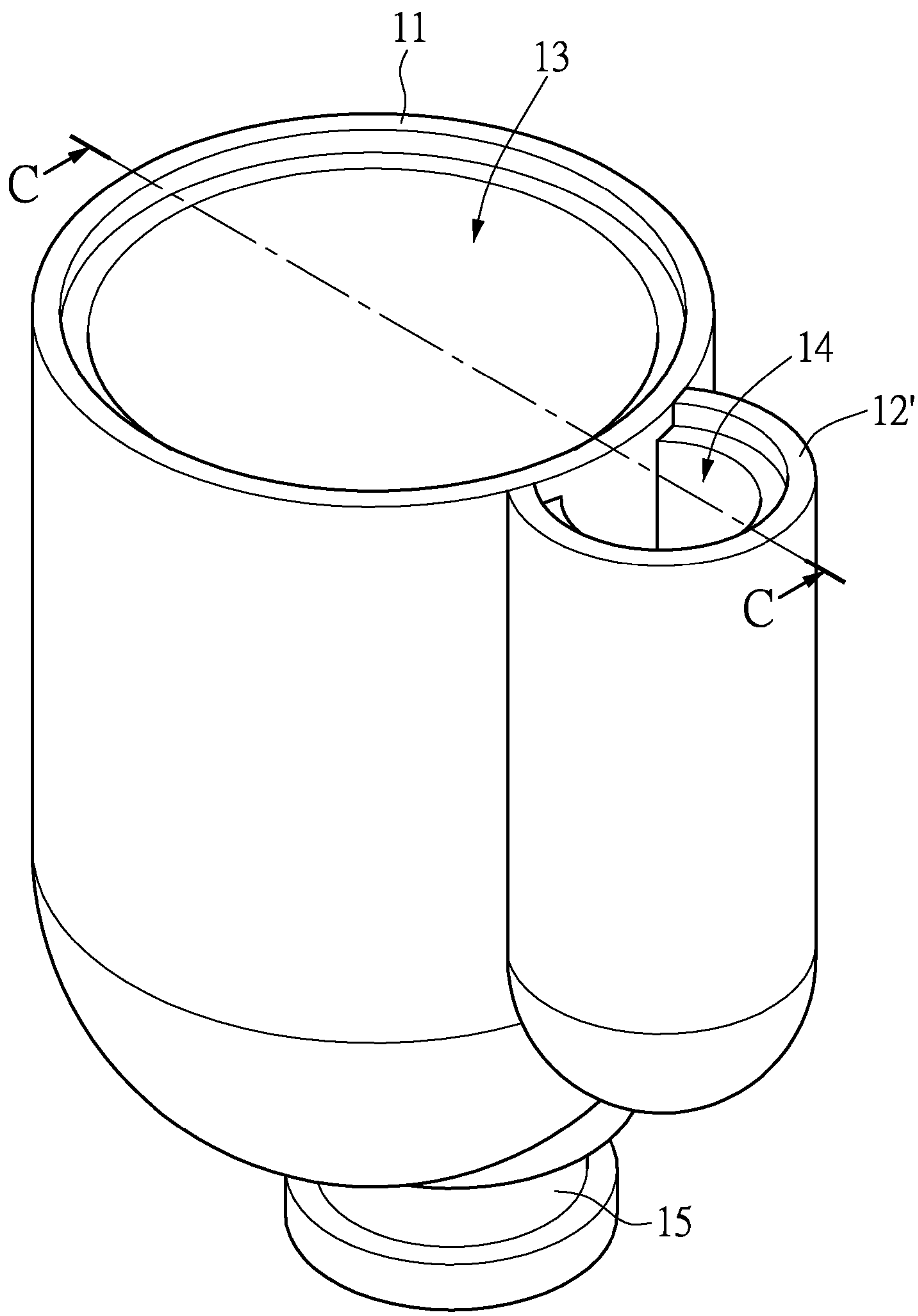
FIG. 8 is a partial perspective view illustrating an embodiment of the in ear headphone of the instant disclosure.

FIG. 8 is a partial perspective view illustrating a second embodiment of the in ear headphone 1'. FIG. 9 is a perspective cross-sectional view along C-C of FIG. 8. FIG. 10 is a schematic cross-sectional view along C-C of FIG. 8. Referring to FIGS. 8, 9 and 10, in the second embodiment, the first wall 11 of the main body 10' defines the chamber 13. The second wall 12' bends around the circumferential portion of the first wall 11 to form the gap 14. The first and second walls 11, 12' collectively form a connection tube 15 toward the direction of the ear canal. In this regard, the chamber 13 opens to the ear canal by an opening 131 while the gap 14 opens to the ear canal by an opening 141. The ear pad 20 sleeves the connection tube 15 through the opening 21. In the second embodiment, the second wall 12' bulges from the first wall 11 such that the fabrication of the in ear headphone can be simplified. The dimension of the gap 14 is defined by the second wall 12' and the size may change according to the configuration of the second wall 12'. The second wall 12' may extend from the first wall 11 and the instant disclosure is not limited thereto.

The speaker 30 is disposed in the chamber 13. The sound generated by the speaker 30 goes through the opening 131, which is defined by the connection tube 15, of the chamber 13 to the opening 21 of the ear pad 20. The ambient sound goes through the gap 14 to the opening 141 defined by the connection tube 15 to the opening 21 of the ear pad 20. That is to say, the sound from the speaker 30 and the ambient go through separate routes, the opening 131 and opening 141 respectively, to the opening 21 of the ear pad and then the ear canal.

Referring to FIG. 5, in the first embodiment, the in ear headphone 1 also includes a dust proof paper 40. The dust proof paper 40 covers one end of the gap 14 which directs toward the surrounding air. The dust proof paper 40 prevents foreign particles from entering the gap 14 or contaminating the in ear headphone 1. However, the dust proof paper 40 is made of air permeable material such that the ambient sound can penetrate the dust proof paper 40. The dust proof paper 40 has an effect of tone tuning. Specifically the dust proof paper 40 allows only a portion of the ambient sound to enter the gap 14 and to the ear canal. In other words, the sound in the ear canal is dominated by the sound from the speaker 30.

Referring to FIG. 1, in the first embodiment, the in ear headphone 1 also includes a tuning paper 60. The tuning paper 60 is annular and has an inner diameter substantially equal to the inner diameter of the sound channel 1211 while an outer diameter substantially equal to the inner diameter of the ring portion 1213. Also, the tuning paper 60 is made of air permeable material. The tuning paper 60 is disposed on the ring portion 1213 such that the tuning paper 60 seals the gap 14 when the gap 14 is defined by the first and second walls 11, 12. When the air flows through the tuning paper 60, the tone of the in ear headphone 1 is changed accordingly.

Referring to FIG. 10, in the second embodiment, the in ear headphone 1 also includes a mobile lid 50. The mobile lid 50 is disposed on one end of the gap 14 which is directed toward the ambient air. The arrangement of the mobile lid 50 determines entry of ambient sound.

In summary, the first wall defines the chamber and the first and second walls collectively define the gap so that the ambient sound can pass through the gap and enter the ear canal without affecting the air pressure in the chamber. The first wall extends to form an inner tube to concentrate the sound and reduce ambient sound interference. The lid covers one end of the chamber with only the aperture to allow cord access such that the chamber is substantially sealed off, and sound leakage is minimized. The tuning paper is disposed on the ring portion, and the air flowing through the gap passes the tuning paper for modifying tone.

The descriptions illustrated supra set forth simply the preferred embodiments of the instant disclosure; however, the characteristics of the instant disclosure are by no means restricted thereto. All changes, alternations, or modifications conveniently considered by those skilled in the art are deemed to be encompassed within the scope of the instant disclosure delineated by the following claims.

What is claimed is:

1. An in ear headphone comprising:

a main body including a first wall and a second wall, the first wall defining a chamber, the first wall and the second wall collectively defining a gap, one end of the gap and one end of the chamber being both directed toward an ear canal of a user, the other end of the gap being directed toward ambient air;

wherein the first and second walls are concentric while have a predetermined distance spaced therebetween, and the first and second walls include at least one connection block connecting therebetween;

wherein the first wall is configured to resemble a cup, the end directed toward the ear canal forms a curved portion, and the curved portion is formed with an outlet;

wherein one end of the second wall that is directed toward the ear canal has a adapter portion, the other end thereof has a tube portion, the adapter portion resembles a funnel and has a sound channel directed toward the ear canal, the other end of the adapter portion is formed with a tapered portion, the curved portion of the first wall is disposed in the tapered portion, the outlet corresponds to one end of the sound channel;

an ear pad corresponding to one end of the gap and the chamber, the ear pad conformingly contacting the ear canal, wherein the ear pad sleeves the sound channel; and a speaker disposed in the chamber.

2. The in ear headphone according to claim 1, wherein one end of the first wall and one end of the second wall, which are both directed toward the ear canal, form a connection tube, the gap and the chamber are each formed with an opening toward the connection tube, and the ear pad sleeves the connection tube.

3. The in ear headphone according to claim 1, further comprising a dust-proof paper disposed on one end of the gap that is directed toward the ambient air.

4. The in ear headphone according to claim 1, wherein the main body includes a lid disposed on one end of the chamber that is directed toward the ambient air.

5. The in ear headphone according to claim 4, wherein the lid is formed with an aperture, and the speaker includes a cord going through the aperture.

6. The in ear headphone according to claim 1, further comprising a mobile lid movably disposed on one end of the gap that is directed toward ambient air.

7. The in ear headphone according to claim 1, wherein the first wall extends from the outlet to form an inner tube directed toward the ear canal, the adapter portion further includes a ring portion arranged between the tapered portion and the sound channel, the inner tube is disposed in the ring portion, and the outer diameter of the inner tube is smaller than the inner diameter of the ring portion.

8. The in ear headphone according to claim 7, wherein the inner diameter of the ring portion is larger than the inner diameter of the sound channel.

9. The in ear headphone according to claim 7, wherein the inner diameter of the inner tube is reduced toward the ear canal.

10. The in ear headphone according to claim 7, further comprising a tuning paper disposed on the ring portion.

* * * * *